(12) United States Patent
Yoo et al.

(10) Patent No.: US 10,215,724 B2
(45) Date of Patent: Feb. 26, 2019

(54) ELECTRONIC DEVICE FOR MEASURING BLOOD SUGAR

(71) Applicant: Samsung Electronics Co., Ltd., Gyeonggi-do (KR)

(72) Inventors: Sung-Sik Yoo, Gyeonggi-do (KR); Yong-Ju Yu, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 644 days.

(21) Appl. No.: 14/797,631

(22) Filed: Jul. 13, 2015

(65) Prior Publication Data

US 2016/0025672 A1  Jan. 28, 2016

(30) Foreign Application Priority Data

Jul. 23, 2014 (KR) .................. 10-2014-0093358

(51) Int. Cl.
*G01N 27/327* (2006.01)
*G01N 33/487* (2006.01)

(52) U.S. Cl.
CPC ... *G01N 27/3273* (2013.01); *G01N 33/48792* (2013.01)

(58) Field of Classification Search
None
See application file for complete search history.

(56) References Cited

U.S. PATENT DOCUMENTS

| 2007/0093786 | A1* | 4/2007 | Goldsmith et al. | |
|---|---|---|---|---|
| 2008/0068932 | A1 | 3/2008 | Mosley | |
| 2013/0345664 | A1* | 12/2013 | Beck | A61M 5/1723 604/504 |
| 2015/0173616 | A1* | 6/2015 | Zajac | H04Q 9/00 340/870.07 |

FOREIGN PATENT DOCUMENTS

| JP | 2006-109894 A | 4/2006 |
|---|---|---|
| KR | 10-2012-0008484 A | 1/2012 |
| KR | 20-2012-0008484 U | 12/2012 |

* cited by examiner

*Primary Examiner* — J. Christopher Ball
(74) *Attorney, Agent, or Firm* — Cha & Reiter, LLC.

(57) ABSTRACT

An operating method of an electronic device may include detecting that a strap with a blood sugar measuring device has been connected to the electronic device, receiving blood sugar related data from the blood sugar measuring device, and executing a health application based on the received data.

16 Claims, 10 Drawing Sheets

ELECTRONIC DEVICE FOR MEASURING BLOOD SUGAR

CLAIM OF PRIORITY

This application claims priority under 35 U.S.C. § 119(a) of a Korean Patent Application filed on Jul. 23, 2014 in the Korean Intellectual Property Office and assigned Serial No. 10-2014-0093358, the entire content of which is hereby incorporated by reference.

BACKGROUND

1. Technical Field

The present disclosure generally relates to an electronic device for measuring blood sugar and an operating method thereof.

2. Description of the Related Art

Increasingly, various functions may be performed by one electronic device. For example, a single electronic device may be multi-functional, performing such functions as, communicating with another electronic device, transmitting or receiving a text message, displaying multimedia content such as, a video or a game, accessing the Internet.

Medical equipment capable of identifying a user's health is widely used. Such equipment is conventionally a stand-alone device that is separate from the above-described electronic device. For example, a blood sugar measuring device that may identify a user's blood sugar at a designated time is extensively used for people with diabetes.

Currently, there is no single, integrated devices that functions both as an electronic device capable of performing various functions (e.g., a smartphone, a smartwatch, and the like) and as a blood sugar measuring device capable of identifying a user's blood sugar.

SUMMARY

Aspects of the present disclosure address at least the above-mentioned problems and/or disadvantages and provide at least the advantages described below.

According to one aspect of the present disclosure, a device and method are provided in which a strap connectable to an electronic device (e.g., a smartwatch) includes a blood sugar measuring device so that a function of identifying a user's blood sugar may be provided in addition to the other functions of the electronic device, thereby enhancing user convenience.

Another aspect of the present disclosure is to provide a device and method in which a strap with a blood sugar measuring device may be easily attached or coupled to an electronic device to measure a user's blood sugar, thereby satisfying various user demands.

In a still further aspect of the present disclosure, a device and method may be provided in which a strip and a blood sugar measuring device for measuring a user's blood sugar may be located inward with respect to the user, thereby protecting user privacy.

Still another aspect of the present disclosure is to provide a device and method in which a user's blood sugar level data from the present time to a designated time in the past may be received from a server, thereby conveniently identifying current and past blood sugar levels.

In accordance with yet another aspect, an operating method of an electronic device may include: detecting that a strap with a blood sugar measuring device has been connected to the electronic device; receiving blood sugar related data from the blood sugar measuring device; and executing a health application based on the received data.

In accordance with still another aspect, an electronic device may include: a communication module that receives blood sugar related data from a blood sugar measuring device; a processor that detects that a strap with the blood sugar measuring device has been connected to the electronic device and executes a health application based on the received data; and a memory that stores data controlled by the processor.

Other aspect, advantages, and salient features of the disclosure will become apparent to those skilled in the art from the following detailed description, which taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
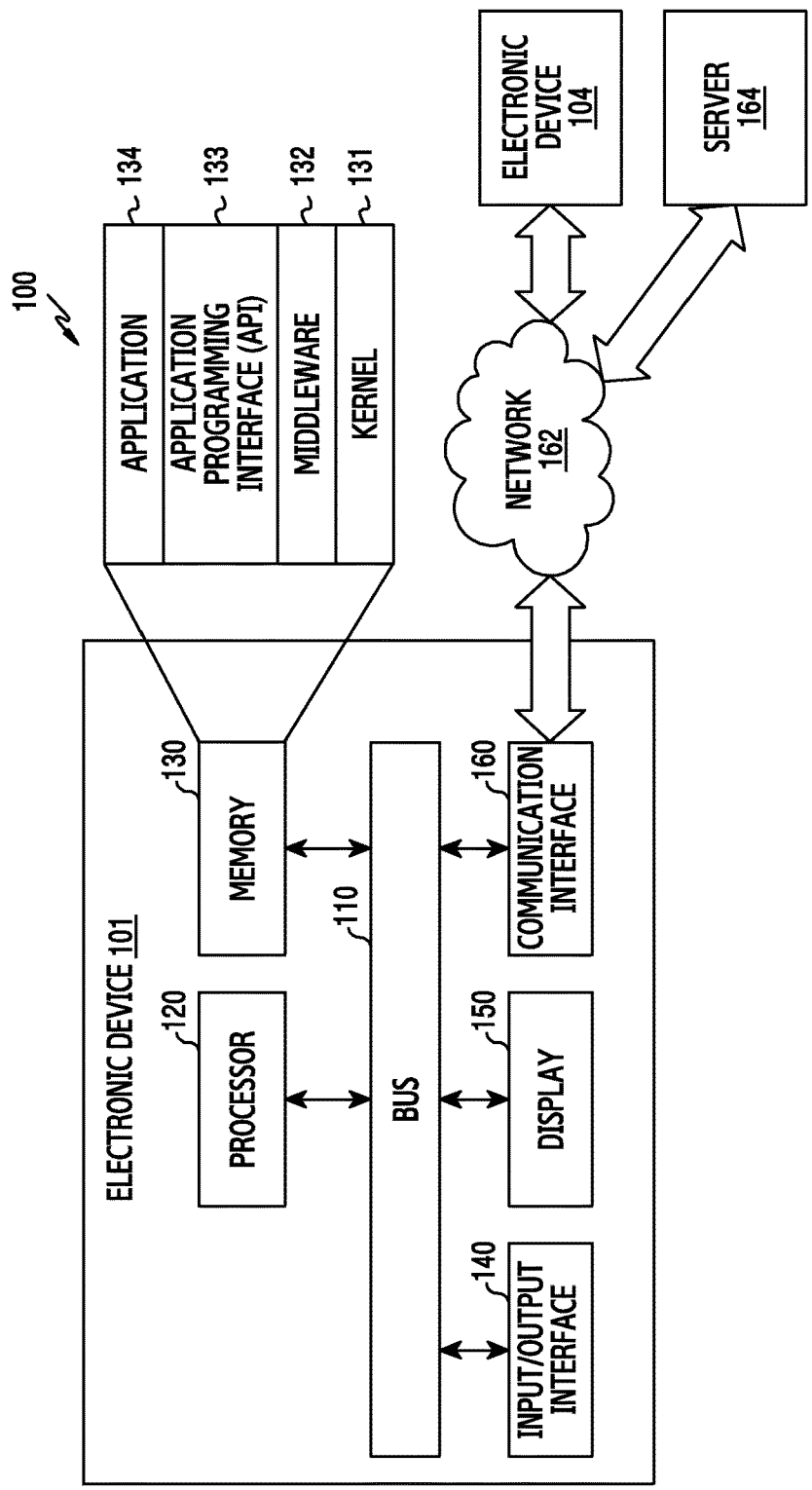
FIG. 1 illustrates a network environment including an electronic device according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to their bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents It is to be understood that the singular forms "a," "an," and "the" include plural referents unless the context clearly dictates otherwise. Thus, for example, reference to "a component surface" includes reference to one or more of such surfaces.

As used in various embodiments of the present disclosure, the expressions "comprise", "may comprise", "include", "may include" and other conjugates refer to the existence of a corresponding disclosed function, operation, or constituent element, and do not limit one or more additional functions, operations, or constituent elements. Further, as used in various embodiments of the present disclosure, the terms "include", "have", and their conjugates are intended merely to denote a certain feature, numeral, step, operation, element, component, or a combination thereof, and should not be construed to initially exclude the existence of or a possibility of addition of one or more other features, numerals, steps, operations, elements, components, or combinations thereof.

Further, as used in various embodiments of the present disclosure, the expression "or" includes any or all combinations of words enumerated together. For example, the expression "A or B" may include A, may include B, or may include both A and B.

While expressions including ordinal numbers, such as "first" and "second", as used in various embodiments of the present disclosure may modify various constituent elements, such constituent elements are not limited by the above expressions. For example, the above expressions do not limit the sequence and/or importance of the elements. The expressions may be used to distinguish a component element from another component element. For example, a first user device and a second user device indicate different user devices although both of them are user devices. For example, a first constituent element may be termed a second constituent element, and likewise a second constituent element may also be termed a first constituent element without departing from the scope of various embodiments of the present disclosure.

It should be noted that if it is described that one component element is "coupled' or "connected" to another component element, the first component element may be directly coupled or connected to the second component, and a third component element may be "coupled" or "connected" between the first and second component elements. Conversely, when one component element is "directly coupled" or "directly connected" to another component element, it may be construed that a third component element does not exist between the first component element and the second component element.

The terms as used in various embodiments of the present disclosure are merely for the purpose of describing particular embodiments and are not intended to limit the various embodiments of the present disclosure. As used herein, the singular forms are intended to include the plural forms as well, unless the context clearly indicates otherwise. Unless defined otherwise, all terms used herein, including technical terms and scientific terms, have the same meaning as commonly understood by a person of ordinary skill in the art to which various embodiments of the present disclosure pertain. Such terms as those defined in a generally used dictionary are to be interpreted to have the meanings equal to the contextual meanings in the relevant field of art, and are not to be interpreted to have ideal or excessively formal meanings unless clearly defined in the present disclosure.

An electronic device according to various embodiments of the present disclosure may be a device including a communication function. For example, the electronic device may include at least one of a smart phone, a tablet personal computer (PC), a mobile phone, a video phone, an e-book reader, a desktop PC, a laptop PC, a netbook computer, a personal digital assistant (PDA), a portable multimedia player (PMP), an MP3 player, a mobile medical device, a camera, a wearable device (e.g., a head-mounted-device (HMD) such as electronic glasses, electronic clothes, an electronic bracelet, an electronic necklace, an electronic appcessory, an electronic tattoo, or a smartwatch).

According to various embodiments, the electronic device may be a smart home appliance with a communication function. The smart home appliance as an example of the electronic device may include at least one of, for example, a television, a Digital Video Disc (DVD) player, an audio, a refrigerator, an air conditioner, a vacuum cleaner, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, and an electronic picture frame.

According to various embodiments, the electronic device may include at least one of various medical appliances (e.g. Magnetic Resonance Angiography (MRA), Magnetic Resonance Imaging (MRI), Computed Tomography (CT) machine, and an ultrasonic machine), navigation devices, Global Positioning System (GPS) receivers, Event Data Recorders (EDRs), Flight Data Recorders (FDRs), automotive infortainment devices, electronic equipments for ships (e.g. navigation equipments for ships, gyrocompasses, or the like), avionics, security devices, head units for vehicles, industrial or home robots, Automatic Teller Machines (ATM) of banking facilities, and Point Of Sales (POSs) of shops.

According to various embodiments, the electronic device may include at least one of a part of furniture or a building/structure having a communication function, an electronic board, an electronic signature receiving device, a projector, and various kinds of measuring instruments (e.g., a water meter, an electric meter, a gas meter, a radio wave meter, and the like). An electronic device according to various embodiments of the present disclosure may be a combination of one or more of above described various devices. Further, the electronic device according to various embodiments of the present disclosure may be a flexible device. Further, it will be apparent to those skilled in the art that the electronic device according to various embodiments of the present disclosure is not limited to the aforementioned devices.

Hereinafter, an electronic device according to various embodiments of the present disclosure will be described with reference to the accompanying drawings. The term "user" as used in various embodiments of the present disclosure may indicate a person who uses an electronic device or a device (e.g., artificial intelligence electronic device) that uses an electronic device.

FIG. 1 illustrates a network environment 100 including an electronic device 101, according to various embodiments of the present disclosure. Referring to FIG. 1, the electronic device 101 may include a bus 110, a processor 120, a memory 130, an input/output interface 140, a display 150, and/or a communication interface 160.

The bus 110 may be a circuit for interconnecting the aforementioned elements and transmitting communication (e.g., a control message) between the aforementioned elements.

For example, the processor 120 may receive instructions from the aforementioned other elements (e.g., the memory 130, the input/output interface 140, the display 150, and/or the communication interface 160) through the bus 110, decode the received instructions, and perform calculation or data processing according to the decoded instructions.

The memory 130 may store instructions and/or data received from or created by the processor 120 or other elements (e.g., the input/output interface 140, the display 150, and the communication interface 160). The memory 130 may include programming modules, for example, a kernel 131, middleware 132, an Application Programming Interface (API) 133, and/or applications 134. The aforementioned programming modules may be formed of software, firmware, hardware, or a combination of two or more thereof.

The kernel 131 may control or manage system resources (e.g., the bus 110, the processor 120, and the memory 130) used for executing an operation or a function implemented in the remaining other programming modules, for example, the middleware 132, the API 133, or the applications 134. In addition, the kernel 131 may provide an interface through which the middleware 132, the API 133, or the applications 134 may access the individual elements of the electronic device 101 to control or manage the same.

The middleware 132 may function as a relay that allows the API 133 or the application 134 to communicate with the kernel 131 to transfer data. Furthermore, in regard to task requests received from the applications 134, the middleware 132 may perform a control (e.g., scheduling or load balancing) for the task requests, using a method of allocating a priority for using the system resources (e.g., the bus 110, the processor 120, and the memory 130) of the electronic device 101 to at least one of the applications 134.

The API 133 is an interface through which the applications 134 may control functions provided by the kernel 131 and the middleware 132, and may include at least one interface or function (e.g., an instruction) for file control, window control, image processing, and/or text control.

According to various embodiments, the applications 134 may include a Short Message Service (SMS)/Multimedia Messaging Service (MMS) application, an email application, a calendar application, an alarm application, a health care application (e.g., application measuring a quantity of exercise or blood sugar) or an environment information application (e.g., application providing information on pressure, humidity, or temperature). Additionally or alternately, the applications 134 may include an application related to an information exchange between the electronic device 101 and an external electronic device (e.g., an electronic device 104). The application 134 may be related to the exchange of information may include, for example, a notification relay application for transferring predetermined information to the external electronic device or a device management application for managing the external electronic device.

For example, the notification relay application may include a function of transferring, to the external electronic device (e.g., the electronic device 104), notification information generated from other applications of the electronic device 101 (e.g., an SMS/MMS application, an e-mail application, a health management application, an environmental information application, and the like). Additionally, or alternatively, the notification relay application may receive notification information from, for example, the external electronic device (e.g., the electronic device 104) and may provide the received notification information to a user. For example, the device management application may manage (e.g., install, delete, or update) functions for at least a part of the external electronic device (e.g., the electronic device 104) communicating with the electronic device 101 (e.g., turning on/off the external electronic device itself (or some elements thereof) or adjusting brightness (or resolution) of a display), applications operating in the external electronic device, or services (e.g., a telephone call service or a message service) provided from the external electronic device.

According to the various embodiments, the applications 134 may include an application designated according to an attribute (e.g., a type) of the external electronic device (e.g., the electronic device 104). For example, in a case where the external electronic device is an MP3 player, the application 134 may include an application related to the reproduction of music. Similarly, in cases where the external electronic device is a mobile medical appliance, the applications 134 may include an application related to health care. According to an embodiment, the applications 134 may include at least one of an application designated to the electronic device 101 and an application received from the external electronic device (e.g., a server 164 or the electronic device 104).

The input/output interface 140 may transfer instructions or data input from a user through an input/output device (e.g., a sensor, a keyboard, or a touch screen) to the processor 120, the memory 130, and the communication interface 160 through, for example, the bus 110. For example, the input/output interface 140 may provide, to the processor 120, data for a user's touch input through the touch screen. In addition, through the input/output device (e.g., a speaker or a display), the input/output interface 140 may output instructions or data received from the processor 120, the memory 130, or the communication interface 160 through the bus 110. For example, the input/output interface 140 may output voice data, processed through the processor 120, to a user through a speaker.

The display 150 may display various pieces of information (e.g., multimedia data or text data) to a user.

The communication interface 160 may connect communication between the electronic device 101 and the external electronic device (e.g., the electronic device 104 or the server 164). For example, the communication interface 160 may be connected to a network 162 through wireless or wired communication to communicate with the external device. The wireless communication may include at least one of, for example, Wi-Fi (Wireless Fidelity), Bluetooth (BT), Near Field Communication (NFC), Global Positioning System (GPS) and cellular communication (e.g., Long Term Evolution (LTE), LTE-A, Code Division Multiple Access (CDMA), Wideband CDMA (WCDMA), Universal Mobile Telecommunication System (UMTS), Wireless Broadband (WiBro), and Global System for Mobile communication (GSM)). The wired communication may include at least one of, for example, a Universal Serial Bus (USB), a High Definition Multimedia Interface (HDMI), Recommended Standard 232 (RS-232), and a Plain Old Telephone Service (POTS).

According to an embodiment, the network 162 may be a communication network. The communication network may include at least one of a computer network, the Internet, the Internet of things, and a telephone network. According to one embodiment, a protocol (e.g., a transport layer protocol, data link layer protocol, or a physical layer protocol) for communicating between the electronic device 101 and the external device may be supported by at least one of the application 134, the application programming interface 133, the middleware 132, the kernel 131, and/or the communication interface 160.

Figure 2:
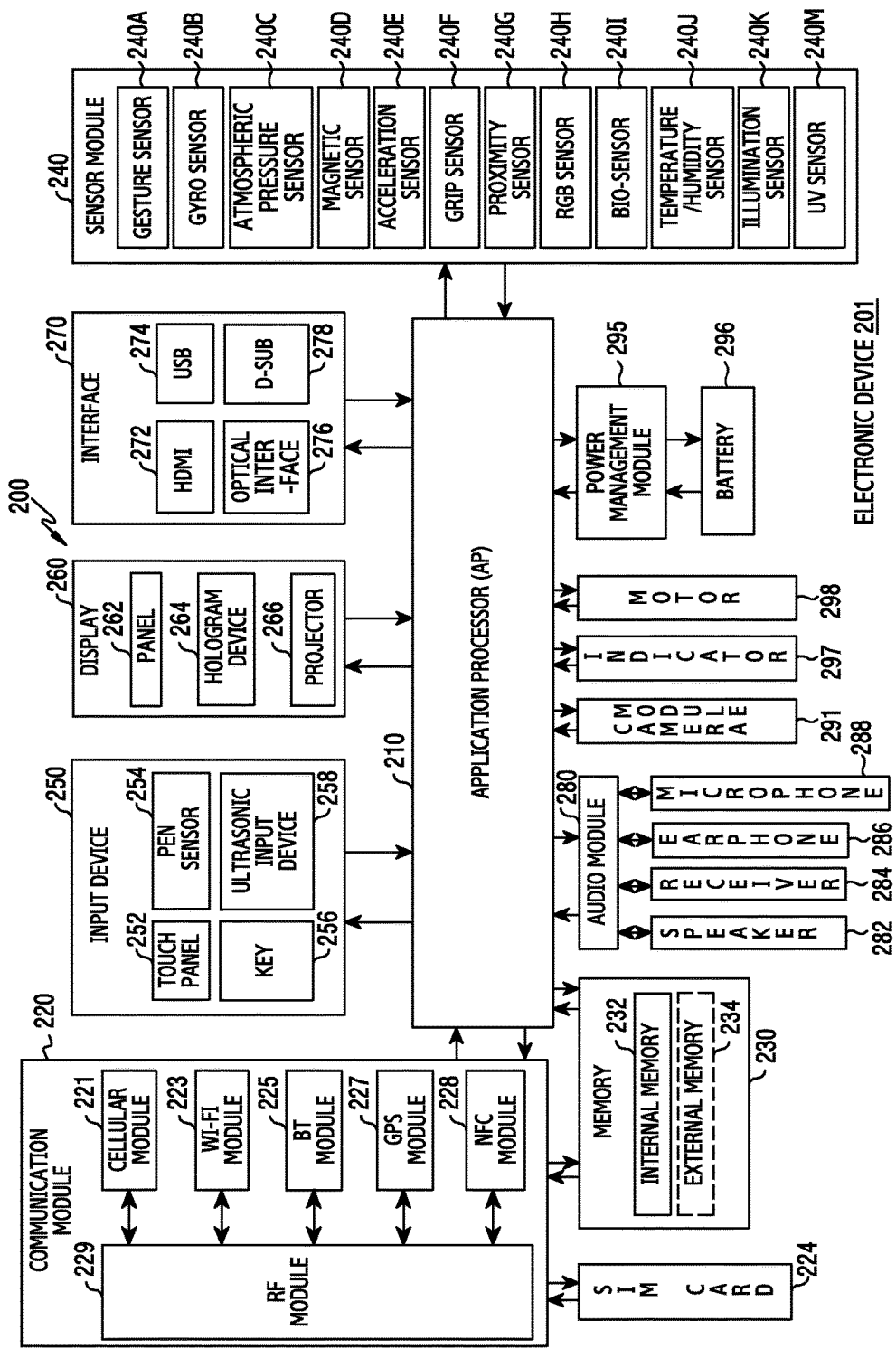
FIG. 2 is a block diagram of an electronic device according to various embodiments of the present disclosure.

FIG. 2 is a block diagram 200 of an electronic device 201 according to various embodiments. The electronic device 201 may configure, for example, the whole or a part of the electronic device 101 illustrated in FIG. 1.

Referring to FIG. 2, the electronic device 201 may include at least one Application Processor (AP) 210, a communication module 220, a Subscriber Identifier Module (SIM) card 224, a memory 230, a sensor module 240, an input device 250, a display 260, an interface 270, an audio module 280, a camera module 291, a power management module 295, a battery 296, an indicator 297, and a motor 298.

The AP 210 may drive an operating system or an application program to control a plurality of hardware or software elements connected thereto and may process and calculate various types of data including multimedia data. The AP 210 may be implemented by, for example, a System on Chip (SoC). According to one embodiment, the AP 210 may further include a Graphic Processing Unit (GPU).

The communication module 220 (e.g., the communication interface 160) may perform data transmission/reception in communication between the electronic device 201 (e.g., the electronic device 101) and other electronic devices (e.g., the electronic device 104 and the server 164) connected thereto through a network. According to an embodiment, the communication module 220 may include a cellular module 221, a Wi-Fi module 223, a BT module 225, a GPS module 227, an NFC module 228, and/or a Radio Frequency (RF) module 229.

The cellular module 221 may provide a voice call, a video call, a Short Message Service (SMS), or an Internet service through a communication network (e.g., LTE, LTE-A, CDMA, WCDMA, UMTS, WiBro, or GSM). Furthermore, the cellular module 221 may distinguish between and authenticate electronic devices within a communication network using, for example, a subscriber identification module (e.g., the SIM card 224). According to one embodiment, the cellular module 221 may perform at least some functions which the AP 210 may provide. For example, the cellular module 221 may perform at least some of the multimedia control functions.

According to one embodiment, the cellular module 221 may include a Communication Processor (CP). Furthermore, the cellular module 221 may be implemented by, for example, an SoC. In FIG. 2, the elements such as the cellular module 221 (e.g., a communication processor), the memory 230, and the power management module 295 are illustrated to be separate from the AP 710. However, according to an embodiment, the AP 210 may be implemented to include at least some of the aforementioned elements (e.g., the cellular module 221).

According to an embodiment, the AP 210 or the cellular module 221 (e.g., communication processor) may load a command or data received from at least one of a non-volatile memory and other elements connected thereto in a volatile memory, and may process the loaded command or data. Furthermore, the AP 210 or the cellular module 221 may store data received from or generated by at least one of other elements in a non-volatile memory.

The Wi-Fi module 223, the BT module 225, the GPS module 227, and the NFC module 228 may include, for example, a processor for processing data transmitted or received through a corresponding module. In FIG. 2, the cellular module 221, the Wi-Fi module 223, the BT module 225, the GPS module 227, and the NFC module 228 are illustrated as separate blocks. However, according to an embodiment, at least some (e.g., two or more) of the cellular module 221, the Wi-Fi module 223, the BT module 225, the GPS module 227, and the NFC module 228 may be included in one integrated chip (IC) or one IC package. For example, at least some of the processors corresponding to the cellular module 221, the Wi-Fi module 223, the BT module 225, the GPS module 227, and the NFC module 228 (e.g., the CP corresponding to the cellular module 221 and the Wi-Fi processor corresponding to the Wi-Fi module 223) may be implemented as one SoC.

The RF module 229 may transmit/receive data, which may be, for example, an RF signal. Although not illustrated in the drawing, the RF module 229 may, for example, include a transceiver, a power amp module (PAM), a frequency filter, a low noise amplifier (LNA), or the like. In addition, the RF module 229 may further include an element for transmitting/receiving electronic waves over free air space in wireless communication, for example, a conductor, a conducting wire, or the like. In FIG. 2, the cellular module 221, the Wi-Fi module 223, the BT module 225, the GPS module 227, and/or the NFC module 228 may share one RF module 229. However, according to an embodiment, at least one of the cellular module 221, the Wi-Fi module 223, the BT module 225, the GPS module 227, and the NFC module 228 may transmit/receive an RF signal through a separate RF module.

The SIM card 224 may be a card including a subscriber identification module, and may be inserted into a slot formed in a particular portion of the electronic device. The SIM card 224 may include unique identification information (e.g., an Integrated Circuit Card IDentifier (ICCID)) and/or subscriber information (e.g., an International Mobile Subscriber IDentity (IMSI)).

The memory 230 (e.g., the memory 130) may include an internal memory 232 or an external memory 234. The internal memory 232 may include, for example, at least one of a volatile memory (e.g., a Dynamic RAM (DRAM), a Static RAM (SRAM), and a Synchronous Dynamic RAM (SDRAM)), and a non-volatile Memory (e.g., a One Time Programmable ROM (OTPROM), a Programmable ROM (PROM), an Erasable and Programmable ROM (EPROM), an Electrically Erasable and Programmable ROM (EEPROM), a mask ROM, a flash ROM, a NAND flash memory, and an NOR flash memory).

According to one embodiment, the internal memory 232 may be a Solid State Drive (SSD). The external memory 234 may further include a flash drive, for example, a Compact Flash (CF), a Secure Digital (SD), a Micro Secure Digital (Micro-SD), a Mini Secure Digital (Mini-SD), an extreme Digital (xD), or a memory stick. The external memory 234 may be functionally connected to the electronic device 201 through various interfaces. According to one embodiment, the electronic device 201 may further include a storage device (or a storage medium) such as a hard disc drive.

The sensor module 240 may measure a physical quantity or detect an operating state of the electronic device 201 and convert the measured or detected information into an electronic signal. The sensor module 240 may include, for example, at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., red, green, and blue (RGB) sensor), a biometric sensor 240I, a temperature/humidity sensor 240J, an illumination sensor 240K, and a Ultra Violet (UV) sensor 240M. Additionally or alternatively, the sensor module 240 may include, for example, an E-nose sensor (not illustrated), an electromyography (EMG) sensor (not illustrated), an electroencephalogram (EEG) sensor (not illustrated), an electrocardiogram (ECG) sensor (not illustrated), an Infrared (IR) sensor, an iris sensor (not illustrated), a fingerprint sensor, and the like. The sensor module 240 may further include a control circuit for controlling at least one sensor involved therein.

The input device 250 may include a touch panel 252, a pen sensor 254, which may be digital, a key 256, or an ultrasonic input device 258. The touch panel 252 may recognize a touch input in at least one of, for example, a capacitive scheme, a resistive scheme, an infrared scheme, and an acoustic wave scheme. Furthermore, the touch panel 252 may further include a control circuit. In the case of the capacitive type, physical contact or proximity recognition is possible. The touch panel 252 may further include a tactile layer. In this case, the touch panel 252 may provide a tactile response to the user.

The pen sensor 254 may be implemented, for example, using the same or a similar method to receiving a user's touch input or using a separate recognition sheet. The key 256 may include, for example, a physical button, an optical key, or a keypad. The ultrasonic input device 258 may identify data by detecting an acoustic wave with a microphone (e.g., microphone 288) of the electronic device 201 through an input unit generating an ultrasonic signal, and may perform wireless recognition. According to an embodiment, the electronic device 201 may receive a user input from an external device (e.g., computer or server) connected thereto using the communication module 220.

The display 260 (e.g., the display 150) may include a panel 262, a hologram device 264, or a projector 266. The panel 262 may be, for example, a Liquid Crystal Display (LCD) and an Active Matrix Organic Light Emitting Diode (AM-OLED) display, and the like. The panel 262 may be implemented so as to be, for example, flexible, transparent, or wearable. The panel 262 may be integrated with the touch panel 252 to configure one module. The hologram device 264 may show a 3D image in the air using interference of light. The projector 266 may project light onto a screen to display an image. The screen may be placed, for example, in the interior or on the exterior of the electronic device 201. According to one embodiment, the display 260 may further include a control circuit for controlling the panel 262, the hologram device 264, and/or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 160 illustrated in FIG. 1. Additionally or alternatively, the interface 270 may include, for example, a Mobile High-definition Link (MHL) interface, a Secure Digital (SD)/Multi-Media Card (MMC) interface, or an Infrared Data Association (IrDA) standard interface.

The audio module 280 may bilaterally convert a sound and an electronic signal. At least some elements of the audio module 280 may be included in, for example, the input/output interface 140 illustrated in FIG. 1. The audio module 280 may process sound information input or output through, for example, the speaker 282, the receiver 284, the earphones 286, or the microphone 288.

The camera module 291 is a device for capturing a still image or a video, and according to an embodiment, may include one or more image sensors (e.g., a front sensor or a rear sensor), a lens (not illustrated), an Image Signal Processor (ISP) (not illustrated), or a flash (not illustrated) (e.g., an LED or xenon lamp).

The power management module 295 may manage power of the electronic device 201. Although not illustrated, the power management module 295 may include, for example, a Power Management Integrated Circuit (PMIC), a charger Integrated Circuit (IC), or a battery or fuel gauge.

The PMIC may be mounted, for example, in integrated circuits or SoC semiconductors. The charging methods may be classified into wired charging and wireless charging. The charger IC may charge a battery and prevent inflow of excessive voltage or excessive current from a charger. According to one embodiment, the charger IC may include a charger IC for at least one of the wired charging method and the wireless charging method. Examples of the wireless charging may include magnetic resonance charging, magnetic induction charging, and electromagnetic charging, and an additional circuit such as a coil loop, a resonance circuit, and a rectifier may be added for the wireless charging.

The battery gauge may measure, for example, a residual quantity of the battery 296, or a voltage, a current, or a temperature during the charging. The battery 296 may store or generate electricity, and may supply power to the electronic device 201 by using the stored or generated electricity. The battery 296 may include, for example, a rechargeable battery or a solar battery.

The indicator 297 may display a particular status of the electronic device 201 or the part (e.g., the AP 210) of electronic device 201, for example, a booting status, a message status, a charging status, and the like. The motor 298 may convert an electrical signal into a mechanical vibration. Although not illustrated, the electronic device 201 may include a processing unit (e.g., a GPU) for supporting mobile TV. The processing device for supporting mobile TV may process media data according to standards such as, for example, a digital multimedia broadcasting (DMB), a digital video broadcasting (DVB) or a media flow.

The aforementioned elements of the electronic device according to various embodiments of the present disclosure may be constituted by one or more components, and the name of the corresponding element may vary with a type of electronic device. The electronic device according to various embodiments of the present disclosure may include at least one of the aforementioned elements. Some elements may be omitted or other additional elements may be further included in the electronic device. Further, some of the components of the electronic device according to the various embodiments of the present disclosure may be combined to form a single entity, and thus, may equivalently execute functions of the corresponding elements prior to the combination.

According to an embodiment, an electronic device may include: a communication module that receives blood sugar related data from a blood sugar measuring device; a processor that detects that a strap with the blood sugar measuring device has been connected to the electronic device and executes a health application based on the received data; and a memory that stores data controlled by the processor.

According to an embodiment, the strap may be replaceable.

According to an embodiment, the blood sugar measuring device may have a set strip inserted therein for absorbing blood.

According to an embodiment, the blood sugar measuring device may analyze blood that is absorbed through a strip inserted therein.

According to an embodiment, the electronic device may further include a display that displays a guide message indicating whether to download the health application when it is detected that the strap has been connected to the electronic device for the first time.

According to an embodiment, the communication module may receive the blood sugar related data from the blood sugar measuring device connected in a wired or wireless manner.

According to an embodiment, the communication module may transmit the blood sugar related data to a Personal Health Recorder (PHR) server by executing the health application and receive analyzed blood sugar related data from the PHR server.

According to an embodiment, the electronic device may further include a processor that analyzes the blood sugar related data received from the PHR server and a display that displays the analyzed blood sugar related data, and displays an alert message as well when it is determined that the analyzed blood sugar related data is higher than a set blood sugar level.

According to an embodiment, the electronic device may further include a display that displays an alert message as well when it is determined that the analyzed blood sugar related data is higher than a set blood sugar level According to an embodiment, the health application may include a blood sugar application.

Figure 3:
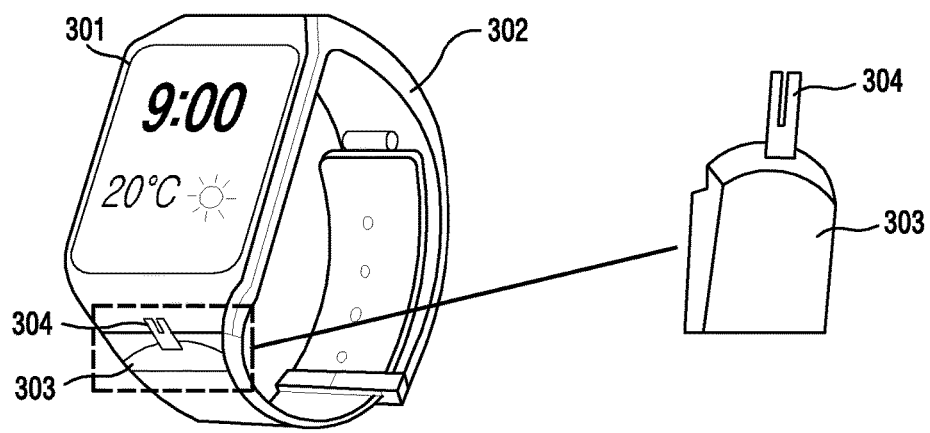
FIG. 3 is a perspective view an electronic device and a strap including a blood sugar measuring device, and an enlarged view thereof shown separated from the strap, according to various embodiments of the present disclosure.

FIG. 3 is a perspective view of an electronic device and a strap according to various embodiments of the present disclosure. According to various embodiments, the electronic device may be a wearable electronic device that may be worn on a user's wrist, shoulder, ankle, or the like. According to an embodiment, the electronic device may transmit/receive a call, a text message, or the like to/from another electronic device, execute a web browser, and/or perform various functions that other typical electronic devices may execute.

According to various embodiments, the strap may be a connecting piece that is connected to the electronic device such that the electronic device may be worn on the user's body. According to an embodiment, in cases where the electronic device is worn on the user's wrist, the strap may function as a watch strap. According to various embodiments, the strap may be of various types, and the electronic device may be designed such that only the strap is replaceable. According to an embodiment, straps having different colors and designs may be selectively connected to the electronic device according to user selection.

According to various embodiments, the electronic device and the strap according to the present disclosure may be designed to measure blood sugar of the user. Hereinafter, an example of the structure of the electronic device and the strap for measuring the user's blood sugar according to the present disclosure will be described with reference to FIG. 3.

According to various embodiments, an electronic device 301 may display a user's blood sugar related data on a display thereof at the same time as performing functions of typical electronic devices. According to an embodiment, the electronic device 301 may receive blood sugar related data from a blood sugar measuring device 303 included in a strap 302 in a wired or wireless manner and execute a blood sugar application. According to an embodiment, the electronic device 301, when receiving the user's blood sugar related data from the blood sugar measuring device 303, may transmit the blood sugar related data to a Personal Health Recorder (PHR) server and then receive the analyzed blood sugar related data from the PHR server. According to an embodiment, the electronic device 301, when receiving the analyzed blood sugar related data from the PHR server, may display the user's current blood sugar level and accumulated blood sugar level on the display thereof.

According to various embodiments, the strap 302 may be designed to be replaceable and may be connected to a set space of the electronic device 301. According to various embodiments, the strap 302 may include the blood sugar measuring device 303, which may measure the user's blood sugar, and/or a strip 304, which may be inserted into the blood sugar measuring device 303 to absorb the user's blood. According to an embodiment, the strip 304 of the blood sugar measuring device 303 may be located in the direction toward the lower end of the electronic device 301 when the electronic device 301 and the strap 302 are connected to each other. According to an embodiment, in cases where the electronic device 301 is worn on the user's wrist, the blood sugar measuring device 303 and the strip 304 are located inward with respect to the user, and therefore, the user's action of measuring the blood sugar may not be exposed to a third party.

According to various embodiments, the blood sugar measuring device 303 may be configured to be included in the strap 302 and may analyze blood supplied from the strip 304 to generate the user's blood sugar related data. According to various embodiments, the blood sugar measuring device 303 may have a separate space into which the strip 304 may be inserted.

According to various embodiments, the strip 304 may function to absorb the user's blood and supply the user's absorbed blood to the blood sugar measuring device 303. According to various embodiments, the strip 304 may be inserted into the separate space in the blood sugar measuring device 303.

Figure 4:
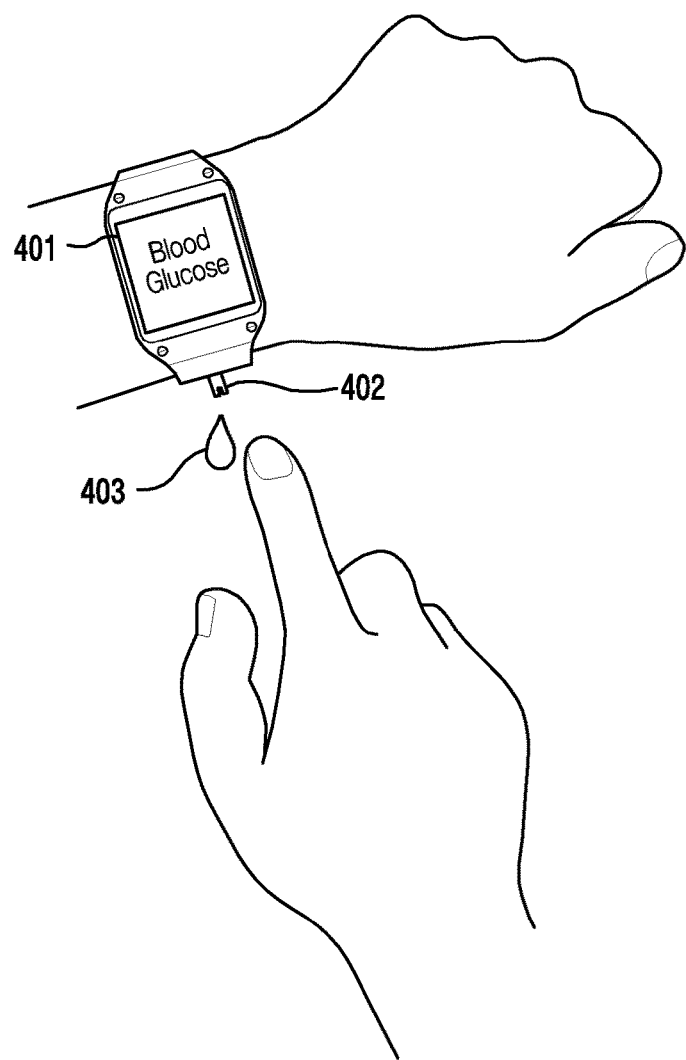
FIG. 4 is a perspective view of an electronic device shown relative to a user's finger illustrating an example of collecting the user's blood according to various embodiments of the present disclosure.

FIG. 4 illustrates an example of collecting a user's blood according to various embodiments of the present disclosure. According to various embodiments, an electronic device may collect data about the user's blood to display the user's blood sugar on a display thereof.

According to various embodiments, a strap detachably coupled to the electronic device may include a blood sugar measuring device that may analyze the user's blood to generate data about the blood and a strip that may be inserted into the blood sugar measuring device to absorb the user's blood. Hereinafter, with reference to FIG. 4, a case will be described in which an electronic device and a strap are connected to each other, the strap includes a blood sugar measuring device, and the blood sugar measuring device has a strip inserted therein.

According to various embodiments, the strip 402 is configured to be rotatable. For example, as shown in FIG. 4, the strip 402 is rotated to extend toward outside, and the strip 402 may absorb blood 403 from a finger of a user having his/her blood taken. Thereafter, the blood sugar measuring device may analyze the user's blood 403 absorbed through the strip 402 and then generate data about the blood.

According to an embodiment, the electronic device 401 and the strip 402 including the blood sugar measuring device are coupled each other, thereby forming an integrated device in similar form to a wrist watch. The integrated device can be worn on the user's wrist, and the strip 402 is disposed around the wrist. The user can rotate the wrist on the wrist similar to an axis. Here, by the rotation of the wrist, the user can use the strip 402 of the integrated device where a third party's eyes won't see it.

Figure 5A:
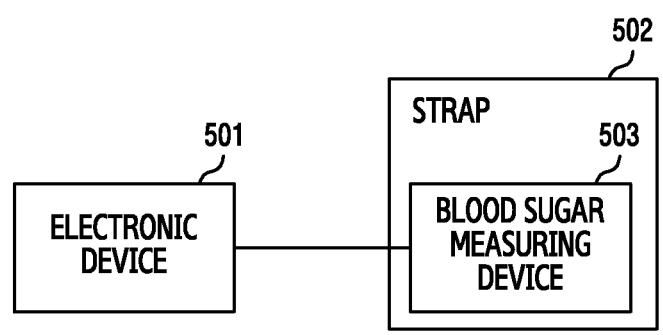
FIG. 5A and FIG. 5B illustrate an example of transmitting/receiving data between an electronic device and a blood sugar measuring device according to various embodiments of the present disclosure.
Figure 5B:
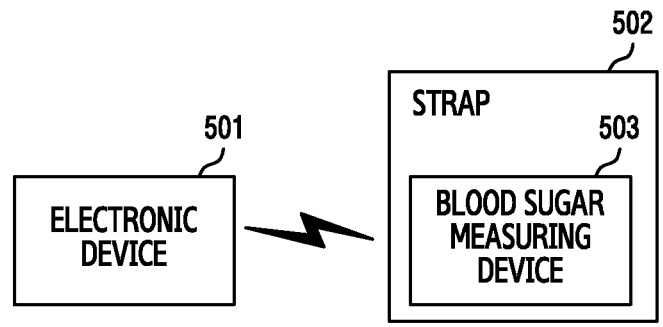

FIGS. 5A and 5B illustrate an example of transmitting/receiving data between an electronic device and a blood sugar measuring device according to various embodiments of the present disclosure. Hereinafter, with reference to FIGS. 5A and 5B, an example will be described in which a blood sugar measuring device collects a user's blood, and then an electronic device 501 receives data about the blood from the blood sugar measuring device 503.

Referring to FIG. 5A, the electronic device 501 (e.g., the electronic device 301) may receive, in a wired manner, data related to a user's blood from a blood sugar measuring device 503 (e.g, the blood sugar measuring device 303) included in a strip 502 (e.g, the strap 302) connected thereto. According to various embodiments, in cases where the electronic device 501 and the strap 502 are connected to each other through a pogo pin, the electronic device 501 may receive the blood related data from the blood sugar measuring device 503 through the pogo pin.

Referring to FIG. 5B, the electronic device 501 may receive, in a wireless manner, data related to a user's blood from a blood sugar measuring device 503 (e.g, the blood sugar measuring device 303) included in a strap 502 (e.g, the strap 302) connected thereto. According to various embodiments, in cases where the electronic device 501 may perform wireless communication, such as Near Field Communication (NFC), with the blood sugar measuring device 503, the electronic device 501 may 30 receive the blood related data from the blood sugar measuring device 503. According to an embodiment, the electronic device 501 may receive the data related to the user's blood from the blood sugar measuring device 503 through short range communication such as Bluetooth, Bluetooth low energy, Zigbee, or the like.

Figure 6A:
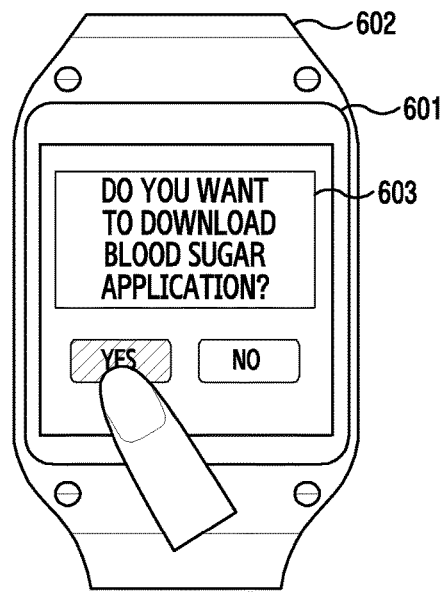
FIG. 6A, FIG. 6B, and FIG. 6C illustrate an example of downloading a blood sugar application according to various embodiments of the present disclosure.
Figure 6B:
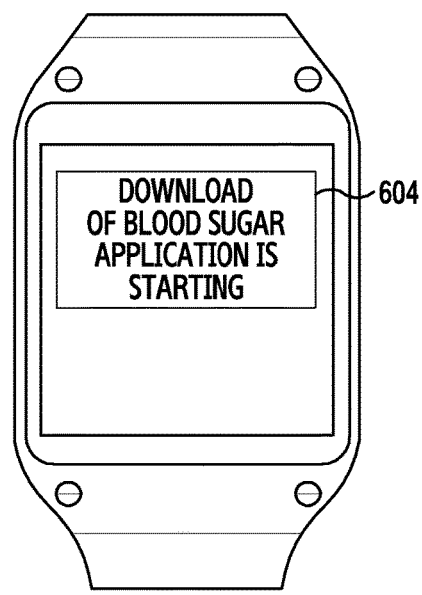
Figure 6C:
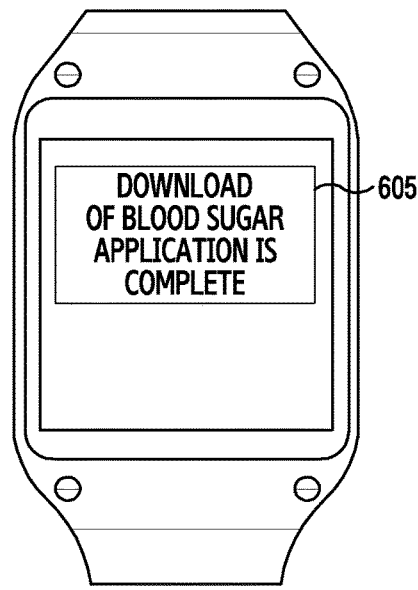

FIGS. 6A to 6C illustrate an example of downloading a blood sugar application according to various embodiments of the present disclosure. According to various embodiments, an electronic device may detect that a strap with a blood sugar measuring device has been connected thereto. According to an embodiment, the electronic device may detect that a typical strap without a blood sugar measuring device has been replaced by a strap with a blood sugar measuring device. For example, as illustrated in FIG. 6, in cases where the strap 602 with the blood sugar measuring device is connected to the electronic device 601, the electronic device 601 may detect that the strap 602 with the blood sugar measuring device has been connected thereto.

According to various embodiments, when the electronic device detects that the strap with the blood sugar measuring device has been connected thereto for the first time, the electronic device may display a guide message indicating whether to download a blood sugar application.

For example, a case will be described in which the electronic device detects that strap A without a blood sugar measuring device has been replaced by strap B with a blood sugar measuring device. In the example, the electronic device, when determining that strap B has been connected thereto for the first time, may display a guide message indicating whether to download a blood sugar application.

In another example, a case will be described in which the electronic device detects that strap C with a blood sugar measuring device has been replaced by strap D with a blood sugar measuring device. In the example, the electronic device, when determining that strap D has been connected thereto for the first time, may display a guide message indicating whether to download a blood sugar application.

According to an embodiment, as illustrated in FIG. 6A, when the electronic device 601 detects that the strap 602 with the blood sugar measuring device has been connected thereto for the first time, the electronic device 601 may display a guide message 603, such as, "Do you want to download a blood sugar application?" on a display thereof. According to another embodiment, although not illustrated in FIG. 6A, the electronic device 601 may also output the guide message (e.g., "Do you want to download a blood sugar application?") using a voice.

According to an embodiment, as illustrated in FIGS. 6A to 6C when the electronic device 601 receives an instruction to download the blood sugar application through a user selection, the electronic device 601 may display a guide message 604 "Download of blood sugar application is starting" and may completed the download of the blood sugar application when a set time passes. According to an embodiment, when the electronic device 601 has completely downloaded the blood sugar application, the electronic device 601 may display a guide message 605 "Download of blood sugar application was completed" on the display thereof.

Figure 7:
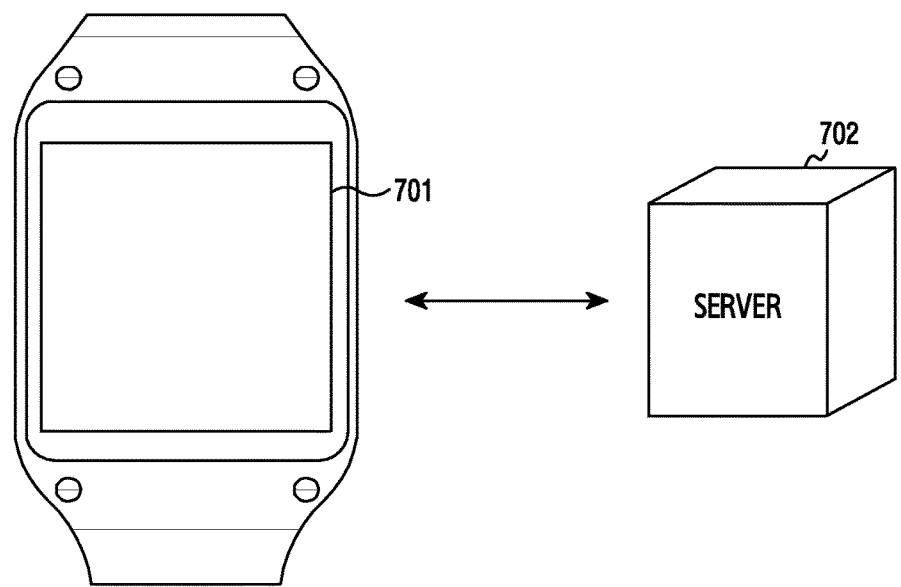
FIG. 7 illustrates an example in which an electronic device, according to various embodiments of the present disclosure, receives blood sugar related data from a server.

FIG. 7 illustrates an example in which an electronic device, according to various embodiments of the present disclosure, receives blood sugar related data from a server. According to various embodiments, when the electronic device receives a user's blood sugar related data from a blood sugar measuring device, the electronic device may transmit the blood sugar related data to a PHR server and then receive the analyzed blood sugar related data from the PHR server. According to an embodiment, the electronic device, when receiving the analyzed blood sugar related data from the PHR server, may display the user's current blood sugar level and accumulated blood sugar level on a display thereof.

For example, as illustrated in FIG. 7, when the electronic device 701 receives the user's blood sugar related data from the blood sugar measuring device included in a strap connected thereto, the electronic device 701 may receive the analyzed blood sugar related data from the PHR server 702.

In the above-described embodiment, the user's blood sugar related data has been accumulated in the PHR server 702, and the user's current blood sugar level and past blood sugar levels for a predetermined period of time may be stored in the PHR server 702. According to an embodiment, when the PHR server 702 receives the user's blood sugar related data from the electronic device 701, the PHR server 702 may analyze the user's current blood sugar and then transmit, to the electronic device 701, the current blood sugar related data and the past blood sugar related data for a predetermined period of time.

According to various embodiments, the electronic device 701 may execute a health application in conjunction with the PHR server 702. According to an embodiment, the health application may be a blood sugar application.

Figure 8C:
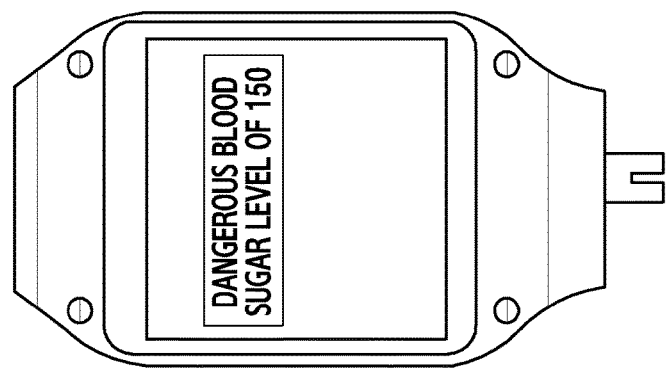
FIG. 8A, FIG. 8B and FIG. 8C illustrate examples of displaying a user's blood sugar related data according to various embodiments of the present disclosure.
Figure 8B:
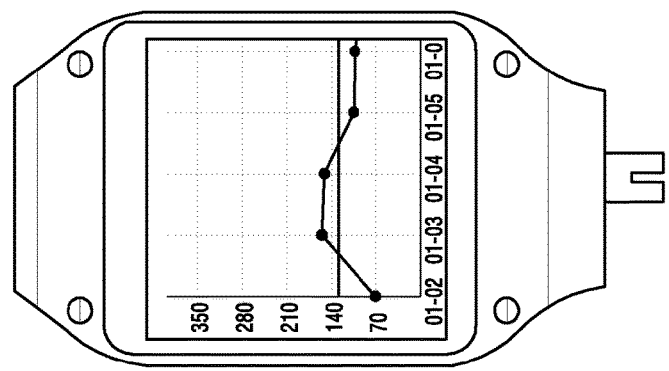
Figure 8A:
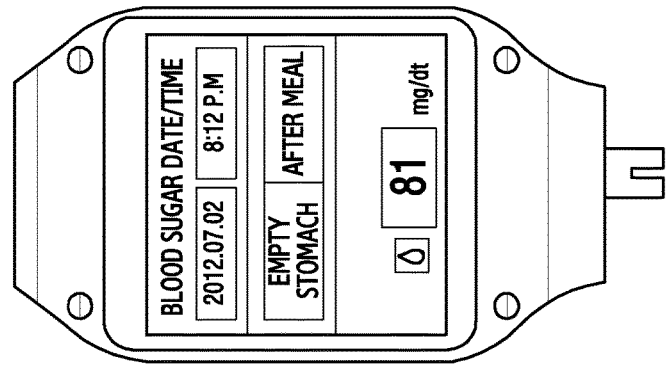

FIGS. 8A-8C illustrate examples of displaying a user's blood sugar related data according to various embodiments of the present disclosure. According to various embodiments, when an electronic device receives the user's blood sugar related data from a PHR server, the electronic device may execute a designated blood sugar application to display various numeric values related to the user's blood sugar. According to an embodiment, when the electronic device receives blood sugar related data from a blood sugar measuring device in a wired or wireless manner, the electronic device may automatically execute the blood sugar application.

According to various embodiments, the electronic device may numerically display the user's current blood sugar level in a set space thereof. For example, as illustrated in FIG. 8A, the electronic device may display a message such as, for example, "At 8:12 P.M. on Jul. 2, 2012, blood sugar level after a meal was 81 mg/dt," on a display thereof.

According to various embodiments, the electronic device may display not only the user's current blood sugar level but also the past blood sugar level after a designated time. For example, as illustrated in FIG. 8B, the electronic device may display blood sugar levels from a designated time to the present time in a graph form on the display thereof.

According to various embodiments, the electronic device, when it is determined that the user's analyzed blood sugar related data is higher than a set blood sugar level, may display an alert message as well. For example, as illustrated in FIG. 8C, when it is determined that the user's current blood sugar level is higher than a set level, the electronic device may display an alert message such as, for example, "dangerous blood sugar level of 150," on the display thereof. Although not illustrated in FIG. 8C, the electronic device may also output the alert message (e.g., "dangerous blood sugar level of 150") using a voice.

Figure 9:
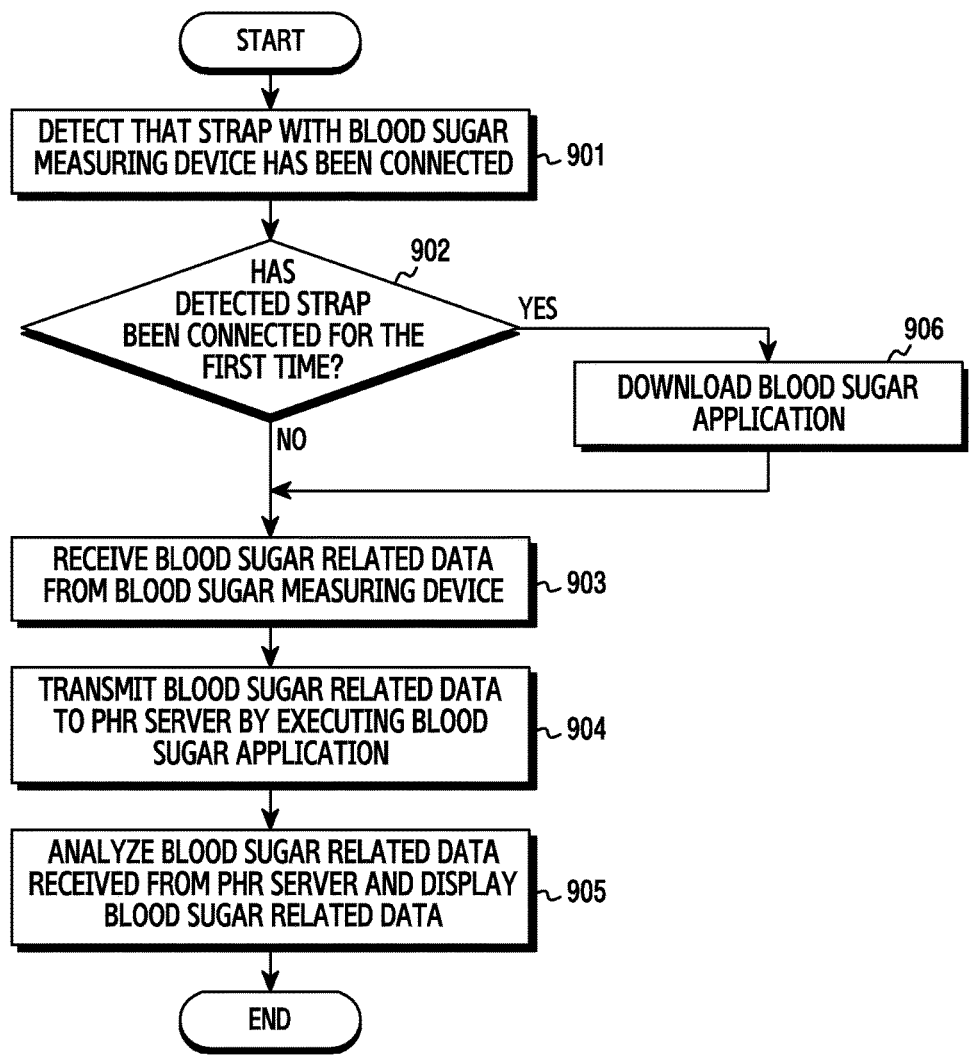
FIG. 9 is a flowchart illustrating an operating sequence of an electronic device according to various embodiments of the present disclosure.

FIG. 9 is a flowchart illustrating an operating sequence of an electronic device according to various embodiments of the present disclosure. As illustrated in FIG. 9, in operation 901, the electronic device may detect that a strap with a blood sugar measuring device has been connected thereto. According to an embodiment, in cases where strap A without a blood sugar measuring device has been replaced by strap B with a blood sugar measuring device, the electronic device may detect that the electronic device and strap B have been connected to each other.

In operation 902, the electronic device may determine whether the detected strap has been connected to the electronic device for the first time. According to an embodiment, in cases where strap C with a blood measuring device has been replaced by strap D with a blood sugar measuring device, the electronic device may determine whether the replacement strap D has been connected to the electronic device for the first time.

In operation 903, the electronic device, when determining that the detected strap does not correspond to the first connected strap, may receive blood sugar related data from the blood sugar measuring device. According to an embodiment, the blood sugar related data may include the user's current blood sugar level analyzed by the blood sugar measuring device.

In operation 904, the electronic device may execute a blood sugar application to transmit the blood sugar related data to a PHR server. According to an embodiment, the user's blood sugar related data has accumulated in the PHR server, and the user's current blood sugar level and past blood sugar levels for a predetermined period of time may be stored in the PHR server.

In operation 905, the electronic device may analyze blood sugar related data received from the PHR server and display the blood sugar related data. According to an embodiment, the electronic device may numerically display the user's current blood sugar level in a set space thereof. In addition, the electronic device may display not only the user's current blood sugar level but also the past blood sugar levels after a designated time, and when it is determined that the user's blood sugar related data is higher than a set blood sugar level, the electronic device may display an alert message as well.

When it is determined in the determination operation 902 that the detected strap has been connected to the electronic device for the first time, the electronic device may download a blood sugar application in operation 906. According to an embodiment, the electronic device may display a guide message (e.g., "Do you want to download a blood sugar application?") on the display thereof. According to another embodiment, when the electronic device receives an instruction to download the blood sugar application through a user selection, the electronic device may display a guide message (e.g., "Download of blood sugar application is starting"), and may complete the download of the blood sugar application when a set time passes.

Figure 10:
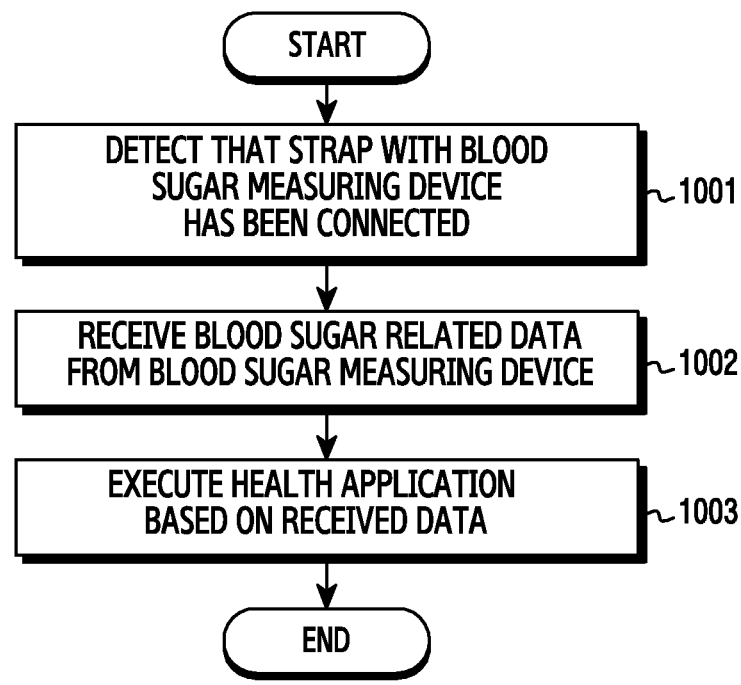
FIG. 10 is a flowchart illustrating an operating method of an electronic device according to various embodiments of the present disclosure.

FIG. 10 is a flowchart illustrating an operating method of an electronic device according to various embodiments of the present disclosure. As illustrated in FIG. 10, in operation 1001, the electronic device may detect that a strap with a blood sugar measuring device has been connected thereto. According to an embodiment, in cases where strap A without a blood sugar measuring device has been replaced by strap B with a blood sugar measuring device, the electronic device may detect that the electronic device and strap B have been connected to each other.

In operation 1002, the electronic device may receive blood sugar related data from the blood sugar measuring device. According to an embodiment, in cases where the electronic device and the strap are connected to each other through a pogo pin, the electronic device receive blood related data from the blood sugar measuring device through the pogo pin. According to an embodiment, in cases where the electronic device may perform wireless communication, such as short range communication, with the blood sugar measuring device, the electronic device may receive the blood related data from the blood sugar measuring device.

In operation 1003, the electronic device may execute a health application based on the received data. According to an embodiment, the health application may be a blood sugar application. According to an embodiment, when the electronic device receives the blood sugar related data from the blood sugar measuring device in a wired or wireless manner, the electronic device may automatically execute the blood sugar application.

According to an embodiment, an operating method of an electronic device may include: detecting that a strap with a blood sugar measuring device has been connected to the electronic device; receiving blood sugar related data from the blood sugar measuring device; and/or executing a health application based on the received data.

According to an embodiment, the strap may be replaceable.

According to an embodiment, the blood sugar measuring device may have a set strip inserted into the device for absorbing blood.

According to an embodiment, the blood sugar measuring device may analyze blood that is absorbed through a strip inserted into the device.

According to an embodiment, the operating method may further include displaying a guide message indicating whether to download the health application when it is detected that the strap has been connected to the electronic device for the first time.

According to an embodiment, the receiving of the blood sugar related data from the blood sugar measuring device may include receiving the blood sugar related data from the blood sugar measuring device connected in a wired or wireless manner.

According to an embodiment, the operating method may further include transmitting the blood sugar related data to a Personal Health Recorder (PHR) server by executing the health application and receiving analyzed blood sugar related data from the PHR server.

According to an embodiment, the operating method may further include analyzing the blood sugar related data received from the PHR server and displaying the analyzed blood sugar related data.

According to an embodiment, the operating method may further include displaying an alert message as well when it is determined that the analyzed blood sugar related data is higher than a set blood sugar level.

According to an embodiment, the health application may include a blood sugar application.

As described above, the various embodiments of the present disclosure may provide a device and method in which a strap connectable to an electronic device includes a blood measuring device so that a function of identifying a user's blood sugar can be provided in addition to functions of the electronic device, thereby enhancing user convenience.

Although specific embodiments have been described in the detailed description of the present disclosure, various change and modifications may be made without departing from the spirit and scope of the present disclosure. Therefore, the scope of the present disclosure should not be defined as being limited to the embodiments, but should be defined by the appended claims and equivalents thereof.

Methods stated in claims and/or specifications according to various embodiments may be implemented by hardware, via the execution of software, or a combination of hardware and software.

In the implementation of software, a computer-readable storage medium for storing one or more programs (software modules) may be provided. The one or more programs stored in the computer-readable storage medium may be configured for execution by one or more processors within the electronic device. The at least one program may include instructions that cause the electronic device to perform the methods according to various embodiments of the present disclosure as defined by the appended claims and/or disclosed herein.

The programs (software modules or software) may be stored in non-volatile memories including a random access memory and a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs), or other type optical storage devices, or a magnetic cassette. Alternatively, any combination of some or all of the may form a memory in which the program is stored. Further, a plurality of such memories may be included in the electronic device.

What is claimed is:

1. An operating method of an electronic device comprising:
   obtaining data from a blood sugar measuring device, wherein the blood sugar measuring device is coupled to a wrist strap connected to the electronic device;
   executing a corresponding application based on the obtained data;
   transmitting the data to a server via the executed application; and
   receiving a response on the transmitted data from the server,
   wherein a blood sugar measuring device generates the data from a blood applied thereto, and the operating method further comprising:
   prompting a user to select whether to download the application associated with blood sugar with a guide message displaying on a display of the electronic device when it is detected that wrist strap is connected to the electronic device for a first time.

2. The operating method of claim 1, wherein the strap is replaceable.

3. The operating method of claim 1, wherein the blood sugar measuring device includes a strip used for blood collection.

4. The operating method of claim 3, wherein the strip is insertable in the blood measuring device.

5. The operating method of claim 1, wherein the data is transmitted to the electronic device wirelessly or in wired.

6. The operating method of claim 1, further comprising:
   displaying, via the display of the electronic device, the response received from the server.

7. The operating method of claim 6, further comprising:
   displaying, via the display, an alert message when the response includes that the data is higher than a set blood sugar level.

8. The operating method of claim 1, wherein the application comprises a blood sugar application.

9. An electronic device comprising:
   a wrist strap connected to the electronic device;
   a blood sugar measuring device coupled to the wrist strap, wherein the blood sugar measuring device generates data from a blood applied thereto; and
   a processor configured to:
     obtain the data from the blood sugar measuring device; and
     executing a corresponding application based on the obtained data;
     transmitting the data to a server via the executed application; and
     receiving a response on the transmitted data from the server,
   wherein the processor is further configured to prompt a user to select whether to download the application associated with a guide message displaying on a display of the electronic device when it is detected that the wrist strap is connected to the electronic device for a first time.

10. The electronic device of claim 9, wherein the strap is replaceable.

11. The electronic device of claim 9, wherein the blood sugar measuring device includes a strip used for blood collection.

12. The electronic device of claim 11, wherein the strip is insertable in the blood measuring device.

13. The electronic device of claim 9, wherein the data is transmitted to the electronic device wirelessly or in wired.

14. The electronic device of claim 9, wherein the processor is further configured to display, via the display of the electronic device, the response received from the server.

15. The electronic device of claim 14, wherein the processor is further configured to display, via the display, an alert message when the response includes that the data is higher than a set blood sugar level.

16. The electronic device of claim 9, wherein the application comprises a blood sugar application.

\* \* \* \* \*